United States Patent [19]

Lindig et al.

[11] Patent Number: 4,845,089
[45] Date of Patent: Jul. 4, 1989

[54] ARTHROPODICIDAL AND FUNGICIDAL METHODS OF USING 1-ARALKYLPYRAZOLES

[75] Inventors: Markus Lindig, Hilden; Benedikt Becker, Mettmann, both of Fed. Rep. of Germany

[73] Assignee: Bayer Aktiengesellschaft, Leverkusen, Fed. Rep. of Germany

[21] Appl. No.: 49,748

[22] Filed: May 13, 1987

[30] Foreign Application Priority Data

May 16, 1986 [DE] Fed. Rep. of Germany ....... 3616681

[51] Int. Cl.$^4$ .............................................. A01N 43/56
[52] U.S. Cl. .................... 514/210; 514/212; 514/326; 514/404; 514/407; 548/362; 548/374; 548/376
[58] Field of Search ............ 548/376, 374, 362; 514/404, 210, 212, 326, 341, 404; 540/362, 524

[56] References Cited

U.S. PATENT DOCUMENTS 4,622,330 11/1986 Bochis et al. ...................... 548/376

OTHER PUBLICATIONS

Substituierte Dithiocarbonsauren und Ketenmercaptale[2,3], Rudolf Gompper und Werner Topfl, Chem. Ber. 95 2861, 2871 (1962).

Primary Examiner—Robert W. Ramsuer
Assistant Examiner—Kurt G. Briscoe
Attorney, Agent, or Firm—Sprung Horn Kramer & Woods

[57] ABSTRACT

1-Aralkylpyrazoles of the formula

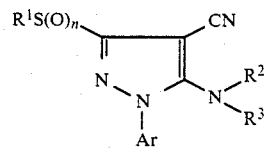

in which
Ar represents optionally substituted aralkyl,
$R^1$ represents alkyl,
$R^2$ represents hydrogen, alkyl, halogenoalkyl, optionally substituted benzyl, or the —$COR^4$, —$COOR^4$, —$NR^5R^6$ or —$CONR^5R^6$ radicals,
where
$R^4$ represents hydrogen, alkyl, halogenoalkyl or alkoxyalkyl, and
$R^5$ and $R^6$ represent hydrogen and/or alkyl,
$R^3$ represents hydrogen or alkyl, or
$R^2$ and $R^3$ together represent the —Co—$(CH_2)_m$—, —$(CH_2)_m$—or —CH=CH—CH=CH— groups,
where
m represents the numbers 2, 3, 4 or 5, and
n represents the numbers 0, 1 or 2, which possess pesticidal activity.

4 Claims, No Drawings

ARTHROPODICIDAL AND FUNGICIDAL METHODS OF USING 1-ARALKYLPYRAZOLES

The present invention relates to new 1-aralkylpyrazoles, several processes for their preparation, their use as pesticides, particularly as acaricides and also to new intermediates for their preparation, and processes for the preparation of these intermediates.

It is already known that pyrazole derivatives, such as, for example, 1-cyclohexyl-5-[N,N-(dimethyl)-carbamoyloxy]-3-methylthiomethyl-pyrazole, 1-cyclohexyl-5-[N,N-(dimethyl)-carbamoyloxy]-3-methylsulphinylmethylpyrazole or 1-cyclohexyl-5-[N,N-(dimethyl)-carbamoyloxy]-3-methylsulphonylmethyl-pyrazole have acaricidal properties (cf., for example, DE-OS (German published specification) No. 2,839,270).

However, the degree of action or the duration of action of these compounds is not always completely satisfactory, particularly in the case of certain spider mite species or in the case of low application concentrations.

New 1-aralkylpyrazoles of the formula (I)

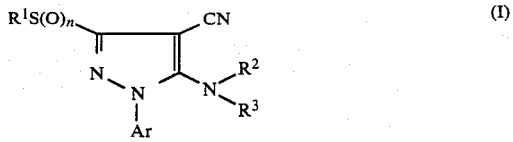

have been found in which
Ar represents optionally substituted aralkyl,
$R^1$ represents alkyl,
$R^2$ represents hydrogen, alkyl, halogenoalkyl, optionally substituted benzyl, or the —$COR^4$, —$COOR^4$, —$NR^5R^6$ or —$CONR^5R^6$ radicals,
where
$R^4$ represents hydrogen, alkyl, halogenoalkyl or alkoxy alkyl, and
$R^5$ and $R^6$ represent hydrogen and/or alkyl,
$R^3$ represents hydrogen or alkyl, or
$R^2$ and $R^3$ together represent the —CO—$(CH_2)_m$—, —$(CH_2)_m$— or —CH=CH—CH=CH— groups,
where
m represents the numbers 2, 3, 4 or 5, and
n represents the numbers 0, 1 or 2.

1-Aralkylpyrazoles of the formula (I)

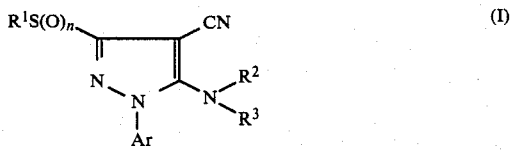

in which
Ar represents optionally substituted aralkyl,
$R^1$ represents alkyl,
$R^2$ represents hydrogen, alkyl, halogenoalkyl, optionally substituted benzyl, or the —$COR^4$, —$COOR^4$, —$NR^5R^6$ or —$CONR^5R^6$ radicals,
where
$R^4$ represents hydrogen, alkyl, halogenoalkyl or alkoxyalkyl, and
$R^5$ and $R^6$ represent hydrogen and/or alkyl,
$R^3$ represents hydrogen or alkyl, or
$R^2$ and $R^3$ together represent the —CO—$(CH_2)_m$—, —$(CH_2)_m$— or —CH=CH—CH=CH— groups,
where
m represents the numbers 2, 3, 4 or 5, and
n represents the numbers 0, 1 or 2,
are obtained from
(a) Compounds of the formula (Ia)

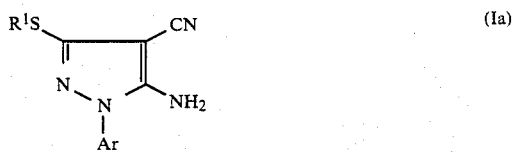

in which $R^1$ and Ar have the meaning given under formula (I), which, in turn as prepared by reaction of Aralkylhydrazines of the formula (II)

in which Ar has the abovementioned meaning, or their acid addition salts, with 1,1-dicyanoethylene derivatives of the formula (III)

in which $R^1$ has the abovementioned meaning, if appropriate in the presence of a solvent, (b) To obtain compounds of the formula (Ib)

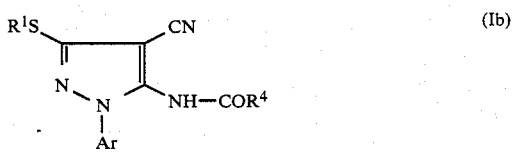

in which Ar, $R^1$ have the meaning specified under formula (I), 1-arylalkyl-4-cyano-5-amino-pyrazoles of the formula (Ia)

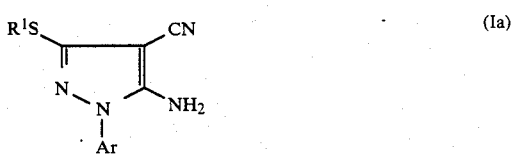

in which Ar and $R^1$ have the abovementioned meaning, are reacted with compounds of the formula

where
X=an activated leaving group (such as alkoxy, OH or halogen).

(c) To obtain compounds of the formula (Ic)

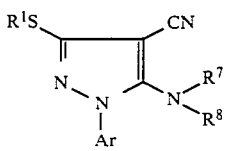
(Ic)

wherein
Ar and $R^1$ have the abovementioned meaning,
$R^7$ represents hydrogen or $-COR^4$, and
$R^8$ represents alkyl,
compounds of the formula (V)

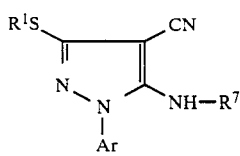
(V)

in which Ar, $R^1$ and $R^7$ have the abovementioned meaning, are reacted with dialkyl sulphate.

(d) To obtain compounds of the formula (Id)

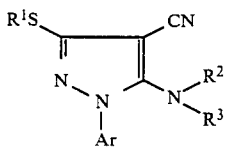
(Id)

in which Ar, $R^1$, $R^2$ and $R^3$ have the meaning specified under formula (I),
1-arylalkyl-4-cyano-5-bromo-pyrazoles of the formula

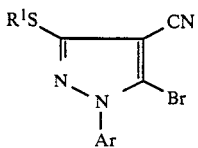
(VI)

in which Ar and $R^1$ have the abovementioned meaning, are reacted with amines of the formula

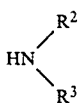
(VII)

(e) To obtain compounds of the formula (Ie)

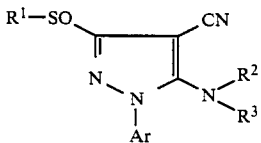
(Ie)

in which Ar, $R^1$, $R^2$ and $R^3$ have the abovementioned meaning,
1-arylalkyl-4-cyano-pyrazoles of the formula (Id)

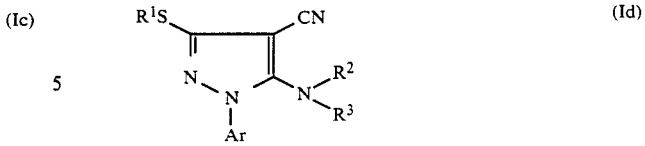
(Id)

in which Ar, $R^1$, $R^2$ and $R^3$ have the abovementioned meaning,
are reacted with equimolar amounts of an oxidant,
(f) To obtain compounds of the formula (If)

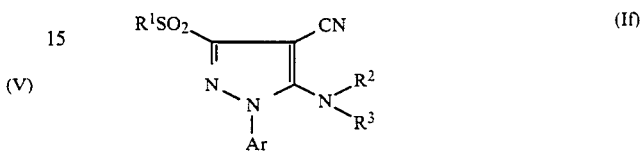
(If)

in which Ar, $R^1$, $R^2$ and $R^3$ have the abovementioned meaning,
1-arylalkyl-4-cyano-pyrazoles of the formula (Id)

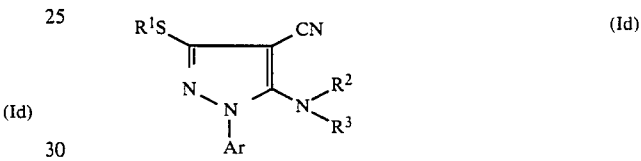
(Id)

are reacted with at least twice the molar amount of an oxidant.

Finally, it has been found that the new 1-aralkylpyrazoles of the general formula (I) have pesticidal and, in particular, acaricidal properties.

Surprisingly, the 1-aralkylpyrazoles, of the general formula (I) according to the invention exhibit a considerably better acaricidal activity than do the pyrazole derivatives, such as, for example, the compounds 1-cyclohexyl-5-[N,N-(dimethyl)-carbamoyloxy]-3-methylthiomethyl-pyrazole, 1-cyclohexyl-5-[N,N-(dimethyl)-carbamoyloxy]-3-methylsulphinylmethyl-pyrazole and 1-cyclohexyl-5-[N,N-(dimethyl)-carbamoyloxy]-3-methylsulphonylmethyl-pyrazole, which are chemically similar compounds and which are known from the prior art.

The 1-aralkylpyrazoles according to the invention are generally defined by the formula (I). Preferred compounds of the formula (I) are those in which Ar represents optionally mono- to trisubstituted phenylalkyl having 1 to 4 carbon atoms in the straight-chain or branched alkyl part, where the substituents are identical or different and the following may be mentioned as substituents of the phenyl radical: Halogen, halogenoalkyl or halogenoalkoxy each preferably having 1 or 2 carbon atoms and 1 to 5 identical or different halogen atoms (particularly fluorine or chlorine), $R^1$ represents alkyl having 1 to 8 carbon atoms, $R^2$ represents hydrogen, $C_1$–$C_8$-alkyl, halogenalkyl having 1 or 2 carbon atoms and 1 to 5 identical or different halogen atoms (particularly fluorine or chlorine), or optionally mono- to trisubstituted benzyl, where the substituents are identical or different and the following may preferably be mentioned as phenyl substituents: Halogen, alkyl having 1 to 4 carbon atoms, and halogenoalkyl having 1 to 2 carbon atoms and 1 to 5 identical or different halogen atoms, and also represents the radicals —COR$^4$, —COOR$^4$, —NR$^5$R$^6$ or —CONR$^5$R$^6$, where R$^4$ represents hydrogen, C$_1$-C$_8$-alkyl, halogenoalkyl having 1 or 2 carbon atoms and 1 to 5 identical or different halogen atoms (particularly fluorine or chlorine), or alkoxyalkyl having 1 to 4 carbon atoms in each alkyl part and where R$^5$ and R$^6$ represent hydrogen or C$_1$-C$_4$-alkyl, R$^3$ represents hydrogen or C$_1$-C$_8$-alkyl, or R$^2$ and R$^3$ together represent the —CO—(CH$_2$)$_m$—, —(CH$_2$)$_m$— or —CH=CH—CH=CH— groups, where m represents the numbers 2, 3, 4 or 5, and n represents the numbers 0, 1 or 2.

Particularly preferred 1-aralkylpyrazoles of the formula (I) are those in which

Ar represents benzyl, 1-phenylethyl or 2-phenylethyl which are in each case optionally mono- or disubstituted, identically or differently, by chlorine or trifluoromethyl, R$^1$ represents alkyl having 1 to 4 carbon atoms, R$^2$ represents hydrogen, C$_1$-C$_4$-alkyl, or optionally mono- or disubstituted benzyl, where the substituents are identical or different and the following may be mentioned as phenyl substituents: Fluorine, chlorine, bromine, methyl, ethyl, isopropyl and trifluoromethyl; and also represents the —NR$^5$R$^6$, —COR$^4$, —COOR$^4$ and —CONR$^5$R$^6$ radicals, R$^4$ represents hydrogen, C$_1$-C$_4$-alkyl, or alkoxyalkyl having 1 to 2 carbon atoms in each alkyl part, and R$^5$ and R$^6$ represent hydrogen or C$_1$-C$_4$-alkyl, R$^3$ represents hydrogen or C$_1$-C$_4$-alkyl, or R$^2$ and R$^3$ together represent the —CO—(CH$_2$)$_m$—, —(CH$_2$)$_m$— or —CH=CH—CH=CH— groups, where m represents the numbers 2, 3, 4, or 5, and n represents the numbers 0, 1 or 2.

The following 1-aralkylpyrazoles of the general formula (I) may be mentioned individually, apart from the compounds mentioned in the preparation examples:

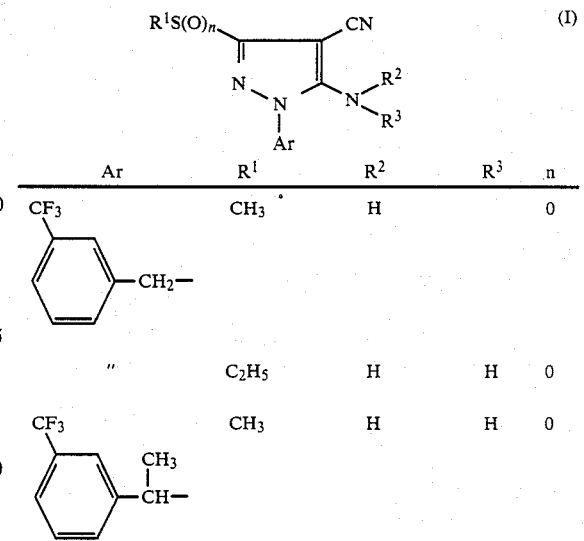

| Ar | R$^1$ | R$^2$ | R$^3$ | n |
|---|---|---|---|---|
| 3-CF$_3$-C$_6$H$_4$-CH$_2$— | CH$_3$ | —NH$_2$ | H | 0 |
| " | CH$_3$ | —NH$_2$ | CH$_3$ | 0 |
| " | CH$_3$ | —COC$_3$H$_7$—i | CH$_3$ | 0 |
| " | CH$_3$ | —COCH$_2$C$_3$H$_7$—i | CH$_3$ | 0 |
| " | CH$_3$ | —COC$_3$H$_7$—i | CH$_3$ | 2 |
| " | CH$_3$ | —CH=CH—CH=CH— | | 1 |
| " | CH$_3$ | —CO—(CH$_2$)$_3$— | | 2 |
| " | CH$_3$ | —COOCH$_3$ | CH$_3$ | 0 |
| " | CH$_3$ | —COOC$_2$H$_5$ | CH$_3$ | 2 |
| " | CH$_3$ | —CON(CH$_3$)$_2$ | CH$_3$ | 0 |
| " | CH$_3$ | —CH$_2$CH$_2$Cl | CH$_3$ | 1 |
| " | CH$_3$ | —CO—(CH$_2$)$_2$— | | 0 |

-continued

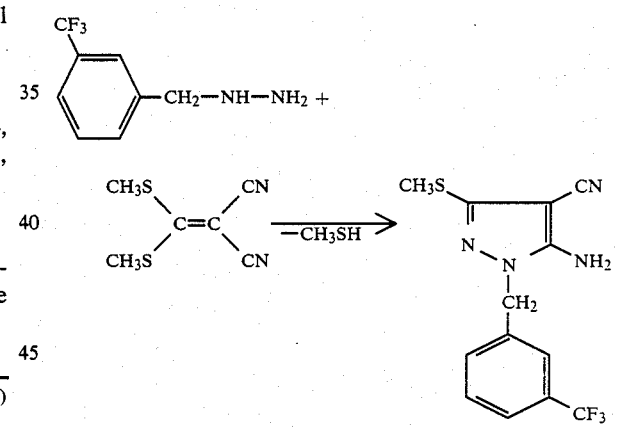

| Ar | R$^1$ | R$^2$ | R$^3$ | n |
|---|---|---|---|---|
| 3-CF$_3$-C$_6$H$_4$-CH$_2$— | CH$_3$ | H | | 0 |
| " | C$_2$H$_5$ | H | H | 0 |
| 3-CF$_3$-C$_6$H$_4$-CH(CH$_3$)— | CH$_3$ | H | H | 0 |

If, for example, 3-trifluoromethyl-benzyl-hydrazine and 1,1-dicyano-2,2-bis-(methylthio)-ethylene are used as starting materials, then the course of the reaction of the process (a) according to the invention may be represented by the following equation:

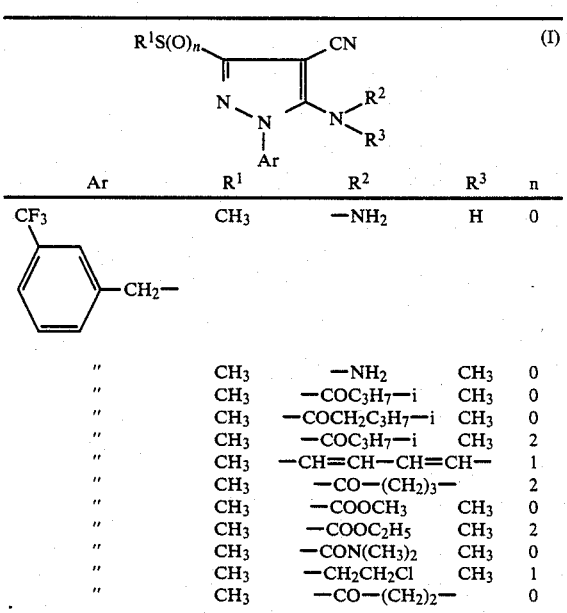

If, for example, 1-(3-trifluoromethylbenzyl)-3-methylmercapto-4-cyano-5-amino-pyrazole and propionyl chloride are used as starting materials, then the course of the reaction of the process (b) according to the invention may be represented by the following equation:

-continued

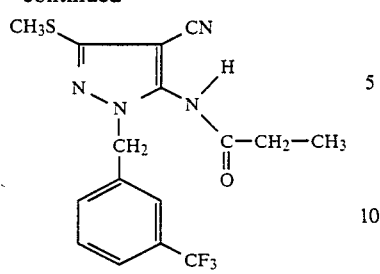

If, for example, 1-(3-trifluoromethylbenzyl)-3-methylmercapto-4-cyano-5-propionylamino-pyrazole and dimethyl sulphate are used as starting materials, then the course of the reaction of the process (c) according to the invention may be represented by the following equation:

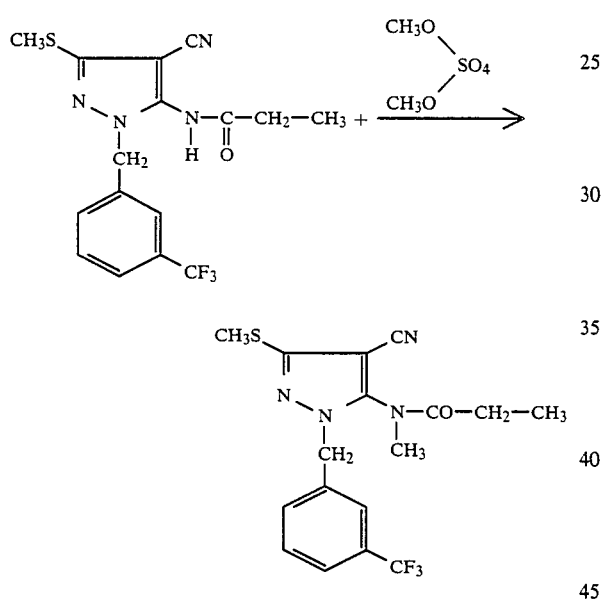

If, for example, 1-(4-trifluoromethylbenzyl)-3-ethylmercapto-4-cyano-5-bromo-pyrazole and dimethylamine are used as starting materials, then the course of the reaction of the process (d) according to the invention may be represented by the following equation:

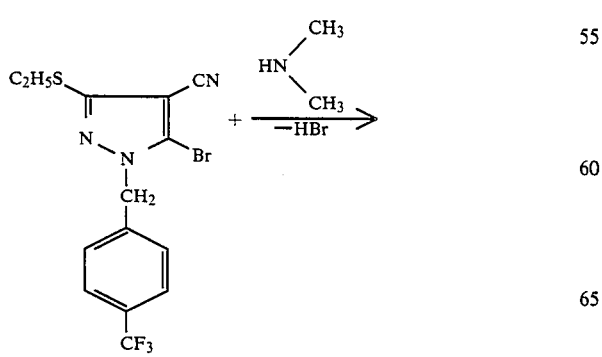

-continued

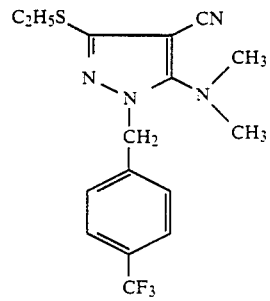

If, for example, 1-(3-trifluoromethylbenzyl)-3-methylmercapto-4-cyano-5-amino-pyrazole and an equimolar amount of 3-chloro-perbenzoic acid are used as starting materials, then the course of the reaction of the process (e) according to the invention may be represented as follows:

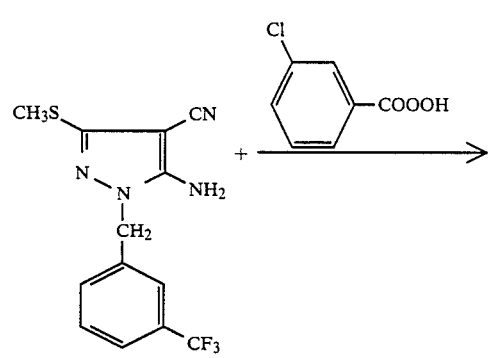

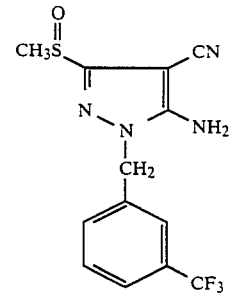

If, for example, 1-(4-trifluoromethylphenyl-ethyl)-3-methylmercapto-4-cyano-5-dimethylamino-pyrazole and twice the molar amount of 3-chloro-perbenzoic acid are used as starting materials, then the course of the reaction of the process (f) according to the invention may be represented as follows:

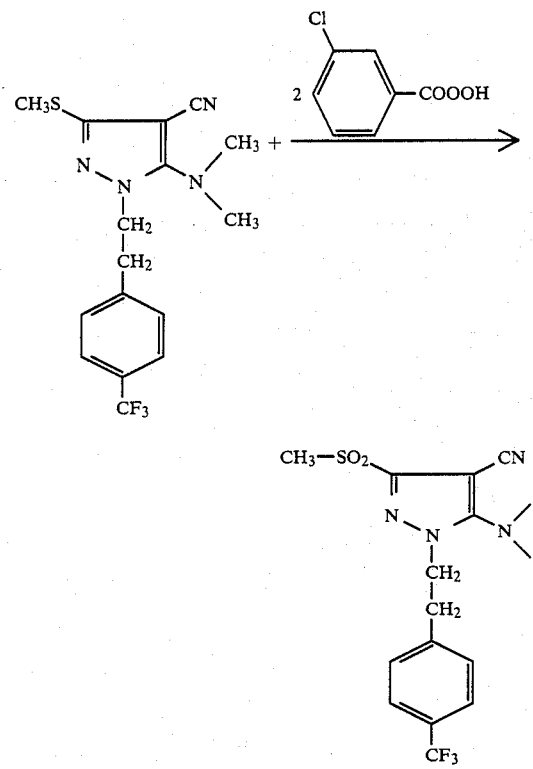

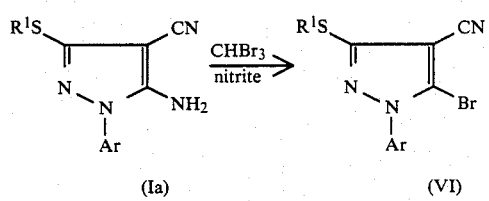
(Ia)  (VI)

The aralkylhydrazines which are required as starting materials for carrying out the process (a) according to the invention are generally defined by the formula (II). In this formula (II), Ar preferably represents those radicals which have already been mentioned in connection with the description of the substances of the formula (I) according to the invention as being preferred for this substituent.

The aralkylhydrazines of the formula (II) are generally known compounds of organic chemistry. The 1,1-dicyanoethylene derivatives of the formula (III) are likewise known (see, for example, Chem. Ber. 95, 2861, 2871 (1962)).

The reaction according to process version (a) is preferably carried out in organic solvents, particularly in alcohols, cyclic ethers (such as tetrahydrofuran), aromatic hydrocarbons (such as benzene and toluene), open-chain ethers (such as diethyl ether) or chlorinated hydrocarbons such as methylene chloride or chloroform. The reaction temperatures are preferably 0° to 60° C., particularly 10° to 30° C. The reaction time is, in general, about 2 to about 20 hours.

In general, molar amounts of the starting components (II) and (III) are mixed together in the solvent and the mixture is stirred at room temperature and atmospheric pressure. The mixture is subsequently concentrated, preferably on a rotary evaporator, and the product is recrystallized from a suitable solvent.

In reaction version (b), the starting compounds of the formula (IV) are generally known compounds of organic chemistry. Suitable here are caboxylates, carboxylic acids and carboxylic acid halides (particularly carboxylic acid chlorides).

The two components (Ia) and (IV) are reacted in a fashion which is conventional per se, preferably in an organic solvent, particularly in cyclic ethers, such as tetrahydrofuran, halogenated hydrocarbons such as methylene chloride or chloroform, acid nitriles such as acetonitrile, or aromatic hydrocarbons such as benzene or toluene. Bases, such as organic amines or, alternatively, pyridine, are preferably added. The reaction temperature is about 0° to about 50° C., the reaction time is about 5 to about 40 hours. Reaction is preferably carried out at atmospheric pressure. Work-up is effected in a conventional fashion, already specified in version (a).

In reaction version (c), molar amounts to a three-fold excess of dialkyl sulphate, known per se, are reacted with the compounds of the formula (V). The reaction is preferably carried out in an organic solvent, particularly in halogenated hydrocarbons such as methylene chloride or chloroform. The reaction temperatures are from about 10° C. to about 40° C., the reaction time is about 2 to about 40 hours.

In this reaction, equivalent amounts of bases, particularly in organic bases such as KOH, NaOH or $Na_2CO_3$, are added. Furthermore, catalysts are added to accelerate the reaction, if necessary. Suitable catalysts are preferably ammonium salts.

The reaction preferably occurs in organic solvents with addition of an aqueous solution of the base and of the dialkyl sulphate. After stirring and concentrating, the product is recrystallized from a suitable organic solvent.

In reaction version (d), the compound of the formula (VI) is reacted with the molar amount to a 20-fold excess of the amine of the formula (VII), preferably without solvents. The reaction temperature is about 0° to about 50° C. and the reaction time is about 5 to about 100 hours. The components are mixed together, the reaction mixture is concentrated after completion of the reaction time, and the reaction product of the formula (Id) is separated off, preferably by column chromatography.

The starting compounds of the formula (VI) employed in the preparation version (d) are new.

They are accessible in a good fashion as follows:

In this reaction, bromoform serves simultaneously as solvent. Tert.-butyl nitrite, isoamyl nitrite or neopentyl nitrite are preferably employed as nitrite, in each case in the molar to 1.5 times the molar amount. The reaction mixture is stirred for 1 to 30 hours at 10° to 30° C., concentrated, taken up in an organic solvent, preferably a halogenated hydrocarbon and particularly in methylene chloride, washed with $NaHCO_3$ solution, separated, dried and concentrated, and, if necessary, the product is recrystallized from a suitable solvent.

A further method for the preparation of the starting compounds of the formula (VI) comprises reacting the pyrazole of the formula Ia as follows:

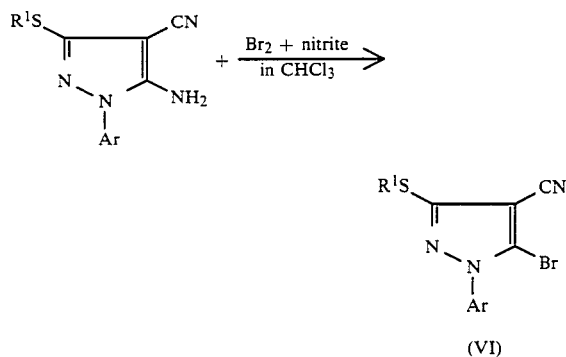

In this reaction, a halogenated hydrocarbon such as chloroform preferably serves as a solvent. The above-mentioned nitrites were employed as nitrites. The one to 1.7 molar amount of each of nitrite and bromine are added oer about 10 to about 30 hours at a temperature of about 10° to about 50° C., the mixture is concentrated, taken up using a chlorinated hydrocarbon, particularly methylene chloride, and shaken with bicarbonate solution (particularly sodium bicarbonate solution), the organic phase is dried and concentrated, and the product, if necessary, is recrystallized from a suitable organic solvent.

In reaction version (e), 1-arylalkyl-4-cyanopyrazoles of the formula (Id) are reacted with an oxidant, preferably with a peracid and particularly with 3-chloroperbenzoic acid. As solvent, polar organic solvents, particularly acetonitrile, methylene chloride or chloroform, were used. The reaction temperature is preferably 0° to 40° C., the reaction duration in general 2 to 25 hours. For the preparation of the sulphoxide (n=1), equimolar amounts of the oxidant, preferably the peracid, are added, whereas an at least 2-molar excess of oxidant (preferably peracid) is required for the preparation of the sulphone (n=2). The reactants are mixed together under the reaction conditions described above. After completion of the reaction, the reaction mixture is concentrated, washed, preferably with an aqueous bicarbonate solution (preferably sodium bicarbonate), and shaken with a polar organic solvent (for example with methylene chloride), and the organic phase is dried and concentrated. The reaction product can be further purified from the concentrated phase by conventional methods (for example crystallization or distillation).

The active compounds are suitable for combating animal pests, particularly arthropods, which are encountered in agriculture, in forestry, in the protection of stored products and of materials, and in the hygiene field exhibiting good plant tolerance and favourable toxicity to warm-blooded animals. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphym avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspitiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia Litura,* Spodoptera spp., Trichoplusiani, *Caprocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna arivestis,* Atomaria spp., *Oryzaephilus surinamensis, Anthonomus spp., Sitophilus spp., Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds also exhibit a good fungicidal activity against *Pyricularia oryzae* on rice.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

Example 1

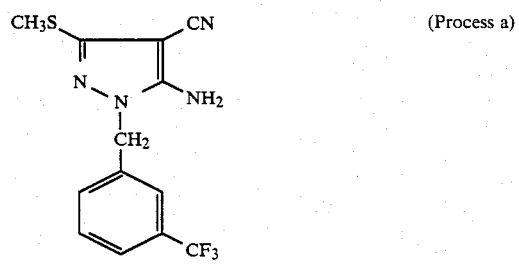

(Process a)

8.5 g of 1,1-dicyano-2,2-bis-(methylmercapto)-ethylene and 9.5 g of 3-trifluoromethyl-benzylhydrazine are mixed in 100 ml of ethanol. The mixture is stirred for 15 hours at 20° C. and the solvent is evaporated in a rotary evaporator. The residue is triturated in petroleum ether. 12.4 g (80% of theory) of 1-(3-trifluoromethylbenzyl)-3-methylmercapto-4-cyano-5-amino-pyrazol of melting point 142° C. are obtained.

Example 2

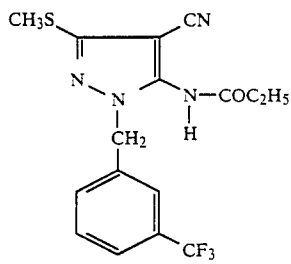
(Process b)

3.2 g of 1-(3-trifluoromethylbenzyl)-3-methylmercapto-4-cyano-5-amino-pyrazole and 2 g of propionyl chloride are dissolved in 50 ml of chloroform, cooled to 0° C., and treated with 1 ml of pyridine. After stirring for 20 hours at 20° C., 50 ml of ethanol is added to the chloroform, the mixture is rendered alkaline using 15 ml of ammonium hydroxide solution (25% strength) and evaporated to dryness, the residue is taken up in chloroform and washed with dilute hydrochloric acid and with water, the chloroform phase is dried using sodium sulphate, and the organic phase is concentrated in a rotary evaporater. Yield: 2.8 g of 1-(3-trifluoromethylbenzyl)-3-methylmercapto-4-cyano-5-propionylamino-pyrazole (76% of theory), Melting point, 181° C.

Example 3

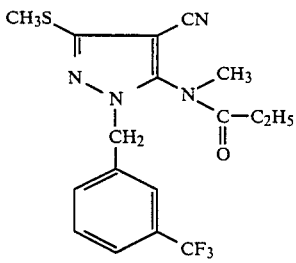
(Process c)

50 ml of a 40% strength aqueous potassium hydroxide solution are added to a solution of 3.7 g of 1-(3-trifluoromethylbenzyl)-3-methyl-mercapto-4-cyano-5-propionylaminopyrazole in 50 ml of chloroform and 0.1 g of tributylbenzylammonium chloride and 1.3 g of dimethyl sulphate. After stirring for 72 hours at 20° C., the organic phase is separated off and washed with water, dried using anhydrous sodium sulphate and concentrated. 3.4 g (90% of theory) of 1-(3-trifluoromethylbenzyl)-3-methylmercapto 4-cyano-5-N-methyl-N-propionyl-amino-pyrazole are obtained as an oily substance.

NMR spectral data 3H 3.1 (s), 2H 1.5–2.1 (m), 3H 0.9 (t).

Example 4

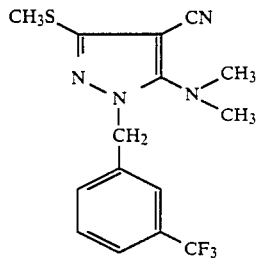
(Process d)

10 ml of dimethylamine are added to 3.8 g of 1-(3-trifluoromethylbenzyl)-3-methylmercapto-4-cyano-5-bromopyrazole, and the mixture is stirred for 72 hours at 20° C. Excess amine is removed in a rotary evaporater and the crude final product is purified via a silica gel column (eluent: mixture of ethyl ether cyclohexane (2:1)).

3.0 g (88% of theory) of 1-(3-trifluoromethylbenzyl)-3-methylmercapto-4-cyano-5-dimethylamino-pyrazole are obtained.

Example 4a

Preparation of the starting material

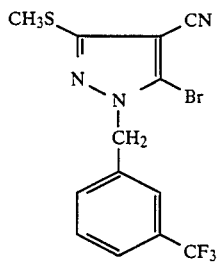

6.7 g of 1-(3-trifluoromethylbenzyl)-3-methylmercapto-4-cyano-5-aminopyrazole and 2.3 ml of tert.-butyl nitrite are stirred for 1 hour in 50 ml of bromoform. Excess bromoform is removed by distillation, the residue is taken up in 50 ml of chloroform and washed with sodium bicarbonate solution, and the organic phase is dried using anhydrous sodium sulphate and subsequently concentrated in a rotary evaporater.

8.2 g (virtually quantitative yield) of 1-(3-trifluoromethylbenzyl-3-methylmercapto-4-cyano-5-bromopyrazole are obtained as an oily substance ($^1$H-NMR: CH$_3$S: 2.6 ppm (s)).

Example 5

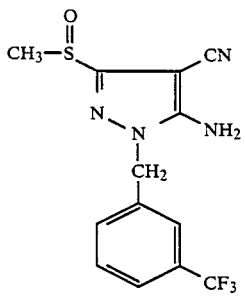
(Process e)

2.7 g of 1-(3-trifluoromethylbenzyl)-3-methylmercapto-4-cyano-5-amino-pyrazole are dissolved in 30 ml of chloroform. A mixture of 1.8 g of 3-chloroperbenzoic acid and 20 ml of chloroform are added dropwise to this solution at 20° C. and stirred for 15 hours. The mixture is subsequently washed with saturated sodium bicarbonate solution, 2% strength sodium thiosulphate solution, and again with saturated aqueous sodium bicarbonate solution. The organic phase is dried using anhydrous sodium sulphate, concentrated, and triturated in petroleum ether. 2.2 g (75% of theory) of 1-(3-trifluoromethylbenzyl)-3-methylsulphinyl-4-cyano-5-aminopyrazole of melting point 143° C. are obtained.

2.7 g of 1-(3-trifluoromethylbenzyl)-3-methylmercapto-4-cyano-5-aminopyrazole are dissolved in 30 ml of chloroform. 3.6 g of 3-chloro-perbenzoic acid dissolved in 20 ml of chloroform are added dropwise to this solution at 20° C. The mixture is stirred for 15 hours. The mixture is subsequently washed with saturated sodium bicarbonate solution, 2% strength sodium thiosulphate solution, and again with saturated aqueous sodium bicarbonate solution. The organic phase is dried using anhydrous sodium sulphate, concentrated, and triturated in petroleum ether. 2.9 g (97% of theory) of 1-(3-trifluoromethylbenzyl)-3-methyl-sulphonyl-4-cyano-5-aminopyrazole of melting point 110° C. are obtained.

The following, inter alia, may be prepared analogously to the abovementioned examples:

Example 6

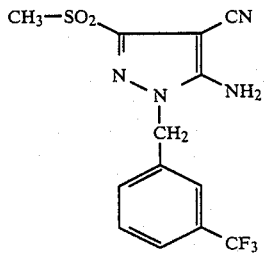

(Process f)

General formula

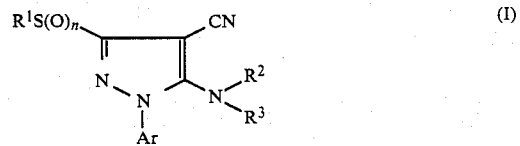

(I)

| Example No. | Preparation version | R$^1$ | n | Ar | R$^2$ | R$^3$ | Physical constants |
|---|---|---|---|---|---|---|---|
| 7 | b | —CH$_3$ | 0 | —CH$_2$—(3,4-diClC$_6$H$_3$) | H | —C(O)—CH$_2$—OC$_2$H$_5$ | M.p. 92° C. |
| 8 | a | —C$_2$H$_5$ | 0 | —CH$_2$—(3-CF$_3$C$_6$H$_4$) | H | H | M.p. 101° C. |
| 9 | a | —CH(CH$_3$)$_2$ | 0 | —CH$_2$—(3-CF$_3$C$_6$H$_4$) | H | H | M.p. 108° C. |
| 10 | a | —CH$_3$ | 0 | —CH$_2$—(4-CF$_3$C$_6$H$_4$) | H | H | M.p. 122° C. |
| 11 | c | —CH$_3$ | 0 | —CH$_2$—(3-CF$_3$C$_6$H$_4$) | H | CH$_3$ | M.p. 159° C. |
| 12 | b | —CH$_3$ | 0 | —CH$_2$—(3-CF$_3$C$_6$H$_4$) | H | —CHO | M.p. 226° C. |
| 13 | a | —CH$_3$ | 0 | —CH$_2$—(3,4-diClC$_6$H$_3$) | H | H | M.p. 145° C. |
| 14 | d | —CH$_3$ | 0 | —CH$_2$—(3-CF$_3$C$_6$H$_4$) | —CH=CH—CH=CH— | | M.p. 64° C. |
| 15 | c | —CH$_3$ | 0 | —CH$_2$—(3-CF$_3$C$_6$H$_4$) | —COCH$_3$ | CH$_3$ | $^1$H—NMR(CDCl$_3$) 3.1 ppm(s) for N—CH$_3$ 2.2 ppm(s) for —CO—CH$_3$ |

-continued

| Example No. | Preparation version | $R^1$ | n | Ar | $R^2$ | $R^3$ | Physical constants |
|---|---|---|---|---|---|---|---|
| 16 | f | —CH₃ | 2 | —CH₂—C₆H₄(CF₃) | CH₃ | CH₃ | M.p. 125° C. |
| 17 | b | —CH₃ | 0 | —CH₂—C₆H₄(CF₃) | —CO—(CH₂)₃— | | M.p. 92° C. |
| 18 | f | —CH₃ | 2 | —CH₂—C₆H₄(CF₃) | —CO—(CH₂)₃— | | M.p. 118° C. |
| 19 | d | —CH₃ | 0 | —CH₂—C₆H₄(CF₃) | CH₃ | C₃H₇—n | ¹H—NMR(CDCl₃) 2.8 ppm(s) for N—CH₃ 0.08 ppm(t) for —CH₂—CH₂—CH₃ 1.5 ppm(m) for —CH₂—CH₂—CH₃ 3.0 ppm(d) for —CH₂—CH₂—CH₃ |
| 20 | d | CH₃ | 0 | —CH₂—C₆H₄(CF₃) | CH₃ | C₂H₅ | ¹H—NMR(CDCl₃) 2.75 ppm(s) for N—CH₃ 1.0 ppm(t) for —CH₂—CH₃ 3.0 ppm(g) for —CH₂—CH₃ |
| 21 | d | CH₃ | 0 | —CH₂—C₆H₄(CF₃) | —CH₂—C₆H₅ | CH₃ | ¹H—NMR(CDCl₃) 2.75 ppm(s) for N—CH₃ 4.2 ppm(s) for —CH₂—C₆H₅ 5.2 ppm (s) —CH₂—C₆H₄—CF₃ |

Example A

Tetranychus test (resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, the following compounds of the preparation examples, for example, exhibit a superior activity compared to the prior art: compounds from Example Nos. 1, 8, 13, 4, 3, 14, 15, 16, 19, 20, 5 and 6.

We claim:

1. A method of combating arthropods which comprises applying to said arthropods, or to a habitat thereof, an arthropodiciadally effective amount of a 1-aralkylpyrazole of the formula

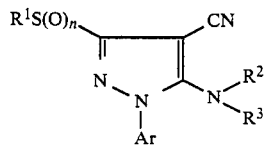

in which

Ar represents optionally substituted phenylalkyl having 1 to 4 carbon atoms in the straight-chain or branched alkyl part, where the substituents on the phenyl radical are selected from the group consisting of halogenoalkyl or halogenoalkoxy each having 1 or 2 carbon atoms and 1 to 5 identical or different halogen atoms, $R^1$ represents alkyl having 1 to 8 carbon atoms, $R^2$ represents hydrogen, $C_1$-$C_8$-alkyl, halogenoalkyl having 1 or 2 carbon atoms and 1 to 5 identical of different halogen atoms, or optionally substituted benzyl, where the substituents on the phenyl are selected from the group consisting of halogen, alkyl having 1 to 4 carbon atoms, and halogenoalkyl having 1 or 2 carbon atoms and 1 to 5 identical or different halogen atoms, and also represents the radicals —COR$^4$, —COOR$^4$, —NR$^5$R$^6$ or —CONR$^5$R$^6$, where R$^4$ represents hydrogen, C$_1$-C$_8$-alkyl, halogenoalkyl having 1 or 2 carbon atoms and 1 to 5 identical or different halogen atoms, or alkoxyalkyl having 1 to 4 carbon atoms in each alkyl part and where R$^5$ and R$^6$ each independently represents hydrogen or C$_1$-C$_4$-alkyl, R$^3$ represents hydrogen or C$_1$-C$_8$-alkyl, or R$^2$ and R$^3$ together represent the —CO—(CH$_2$)$_m$—, —(CH$_2$)$_m$— or —CH=CH—CH=CH— groups, where m represents the numbers 2, 3, 4 or 5, and n represents the numbers 0, 1 or 2.

2. A method according to claim 1 wherein

Ar represents benzyl, 1-phenylethyl or 2-phenylethyl which are in each case optionally substituted by chlorine or trifluoromethyl, R$^1$ represents alkyl having 1 to 4 carbon atoms, R$^2$ represents hydrogen, C$_1$-C$_4$-alkyl, or optionally substituted benzyl, where the phenyl substituents are selected from the group consisting of fluorine, chlorine, bromine, methyl, ethyl, isopropyl and trifluoromethyl; and also represents the —NR$^5$R$^6$, —COR$^4$, —COOR$^4$ and —CONR$^5$R$^6$ radicals, where R$^4$ represents hydrogen, C$_1$-C$_4$-alkyl, or alkoxyalkyl having 1 to 2 carbon atoms in each alkyl part, and R$^5$ and R$^6$ each independently represent hydrogen or C$_1$-C$_4$-alkyl, R$^3$ represents hydrogen or C$_1$-C$_4$-alkyl, or R$^2$ and R$^3$ together represent the —CO—(CH$_2$)$_m$—, —(CH$_2$)$_m$— or —CH=CH—CH=CH— groups, where m represents the numbers 2, 3, 4 or 5, and n represents the numbers 0, 1 or 2.

3. A method of combating fungus comprising applying to said fungus or a habitat thereof a fungicidally effective amount of a 1-aralkylpyrazole of the formula

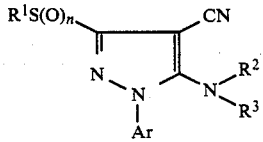

in which

Ar represents optionally substituted phenylalkyl having 1 to 4 carbon atoms in the straight-chain or branched alkyl part, where the substituents on the phenyl radical are selected from the group consisting of halogenoalkyl or halogenoalkoxy each having 1 or 2 carbon atoms and 1 to 5 identical or different halogen atoms, R$^1$ represents alkyl having 1 to 8 carbon atoms, R$^2$ represents hydrogen, C$_1$-C$_8$-alkyl, halogenoalkyl having 1 or 2 carbon atoms and 1 to 5 identical or different halogen atoms, or optionally substituted benzyl, where the substituents on the phenyl are selected from the group consisting of halogen, alkyl having 1 to 4 carbon atoms, and halogenoalkyl having 1 to 2 carbon atoms and 1 to 5 identical or different halogen atoms, and also represents the radicals —COR$^4$, —COOR$^4$, —NR$^5$R$^6$ or —CONR$^5$R$^6$, where R$^4$ represents hydrogen, C$_1$-C$_8$-alkyl, halogenoalkyl having 1 to 2 carbon atoms and 1 to 5 identical or different halogen atoms, or alkoxyalkyl having 1 to 4 carbon atoms in each alkyl part and where R$^5$ and R$^6$ each independently represents hydrogen or C$_1$-C$_4$-alkyl, R$^3$ represents hydrogen or C$_1$-C$_8$-alkyl or R$^2$ and R$^3$ together represent the —CO—(CH$_2$)$_m$—, —(CH$_2$)$_m$— or —CH=CH—CH=CH— groups, where m represents the numbers 2, 3, 4 or 5, and n represents the numbers 0, 1 or 2.

4. A method according to claim 3 wherein

Ar represents benzyl, 1-phenylethyl or 2-phenylethyl which are in each case optionally substituted by chlorine or trifluoromethyl, R$^1$ represents alkyl having 1 to 4 carbon atoms, R$^2$ represents hydrogen, C$_1$-C$_4$-alkyl, or optionally substituted benzyl, where the phenyl substituents are selected from the group consisting of fluorine, chlorine, bromine, methyl, ethyl, isopropyl and trifluoromethyl; and also represents the —NR$^5$R$^6$, —COR$^4$, —COOR$^4$ and —CONR$^5$R$^6$ radicals, where R$^4$ represents hydrogen, C$_1$-C$_4$-alkyl, or alkoxyalkyl having 1 to 2 carbon atoms in each alkyl part, and R$^5$ and R$^6$ each independently represent hydrogen or C$_1$-C$_4$-alkyl, R$^3$ represents hydrogen or C$_1$-C$_4$-alkyl, or R$^2$ and R$^3$ together represent the —CO—(CH$_2$)$_m$—, —(CH$_2$)$_m$— or —CH=CH—CH=CH— groups, where m represents the numbers 2, 3, 4 or 5, and n represents the numbers 0, 1 or 2.

* * * * *